United States Patent [19]

Gobin

[11] Patent Number: 5,020,529
[45] Date of Patent: Jun. 4, 1991

[54] RESUSCITATION DEVICE WITH FILTER

[76] Inventor: Phil L. Gobin, 601 Winterset Pky., Marietta, Ga. 30067

[21] Appl. No.: 451,602

[22] Filed: Dec. 18, 1989

[51] Int. Cl.$^5$ .................... A61M 16/00; A61M 15/00
[52] U.S. Cl. ........................ 128/202.28; 128/203.21; 128/205.13; 128/909
[58] Field of Search .................. 128/202.28, 202.29, 128/203.11, 201.11, 207.14, 203.21, 205.13, 909

[56] References Cited

U.S. PATENT DOCUMENTS

| 3,057,347 | 10/1962 | McGee | 128/202.28 |
| 3,124,124 | 3/1964 | Cross | 128/203.11 |
| 4,090,511 | 5/1978 | Gray | 128/207.14 |

FOREIGN PATENT DOCUMENTS

| 646890 | 8/1962 | Canada | 128/202.29 |
| 1600919 | 9/1970 | France | 128/202.28 |
| 2198958 | 6/1988 | United Kingdom | 128/202.28 |

*Primary Examiner*—Edgar S. Burr
*Assistant Examiner*—Kimberly L. Asher
*Attorney, Agent, or Firm*—Leon Gilden

[57] ABSTRACT

A device is set forth defined by an upper angular mouthpiece including diametrically opposed flexible projections positioned on opposed edges of the mouthpiece for grasping by teeth of an administrator of the device. A first conduit is orthogonally oriented relative to the angular mouthpiece directed to a convex abutment skirt for engagement and positioning of a victim's mouth during use. A replaceable filter is removably mounted between the upper conduit and the skirt. A lower conduit in communication with the first conduit and filter and axially aligned therewith is of a generally arcuate "L" shaped configuration tapering downwardly to a lower opening. A modified filter for use with the invention includes a flexible squeeze bulb with a conduit associating the bulb with a filter, wherein the squeeze bulb includes a rupturable diaphragm containing a germicidal fluid therewith for directing the fluid onto the filter prior to use of the device. A further modified device includes an aspiration bulb of a generally pear shaped configuration formed with a tapered forward surface and a forward outlet for positioning within the mouthpiece to enable directing of pressurized air from the bulb through the first conduit, filter, and lower conduit into a victim.

3 Claims, 4 Drawing Sheets

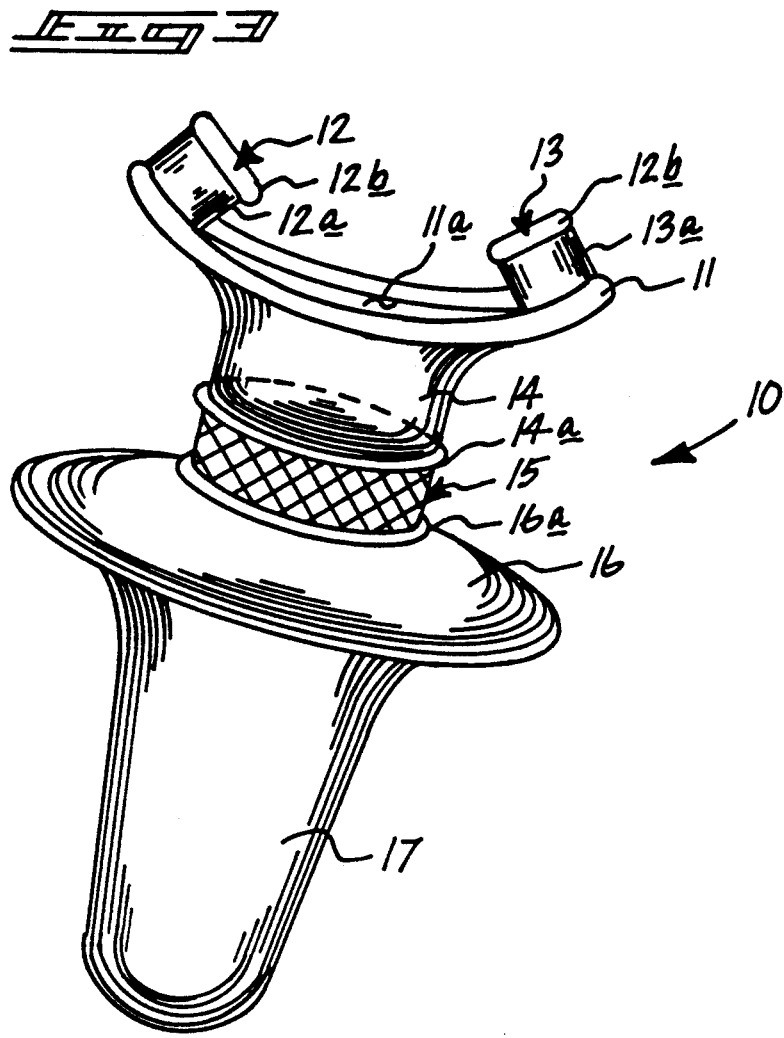
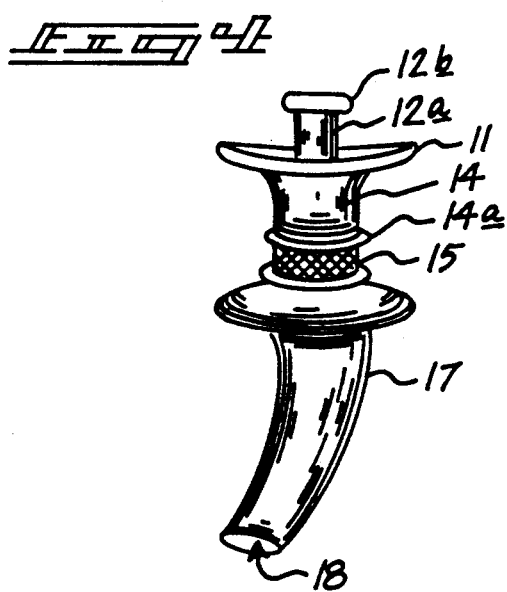

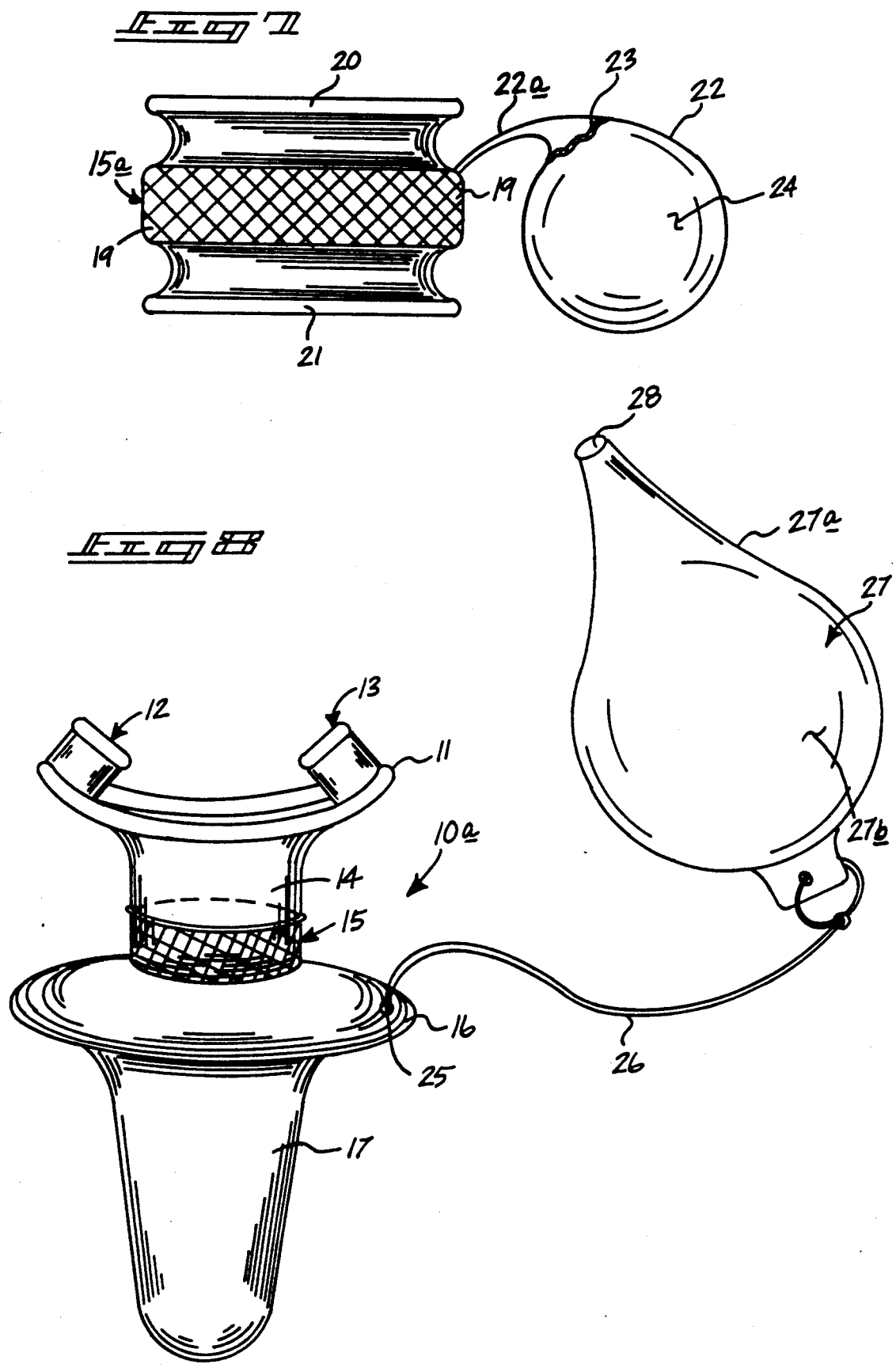

RESUSCITATION DEVICE WITH FILTER

BACKGROUND OF THE INVENTION

1. Field of the Invention

The field of invention relates to resuscitation devices, and more particularly pertains to a new and improved resuscitation device typically utilized in CPR or mouth-to-mouth resuscitation.

2. Description of the Prior Art

Prior art is available in use of resuscitation devices that may be employed to administer artificial breathing to a victim in an effort to revive such an individual. In contemporary environments, the risk of contracting various communicable diseases and viruses has created a reluctance to employ such life-saving procedures to unknown victims due to fear of contracting such diseases. Examples of the prior art include U.S. Pat. No. 3,508,543 to Aulicono setting forth a mouth-to-mouth type resuscitation device wherein a single conduit, including a medially projecting flange positioned exteriorly of the conduit, includes a plurality of nozzles directed to the upper portion of the conduit above the flange for positioning interiorly of an individual's nostrils during a CPR type procedure.

U.S. Pat. No. 4,559,940 to McGinnis sets forth a resuscitation device including an angular cap member to overlie an individual's mouth and nostrils including a construction of a main resuscitation tube to minimize closure thereof during a CPR type procedure.

U.S. Pat. No. 3,802,428 to Sherman sets forth a mouth-to-mouth resuscitation device including a mask for securement to an administrator of the device with a central nozzle directed from an annular disk positioned adjacent an upper end of the nozzle.

U.S. Pat. No. 3,303,845 to Detmer sets forth a resuscitation device with a central convex flange, an upper nozzle, and a fork-like lower member to maintain an individual's tongue in a desired orientation during the CPR procedure.

U.S. Pat. No. 3,057,347 to McGee sets forth a breathing device including an upper tube, a central flange, and lower arcuate tube for directing interiorly of an individual of unitary construction.

As such, it may be appreciated that there is a continuing need for a new and improved resuscitation device wherein the same addresses both the problems of ease of use and effectiveness in construction and in this respect, the present invention substantially fulfills this need.

SUMMARY OF THE INVENTION

In view of the foregoing disadvantages inherent in the known types of resuscitation devices now present in the prior art, the present invention provides a resuscitation device wherein the same includes a replaceable filter positioned above and adjacent an annular skirt utilized with the device to maintain an individual's mouth and lips in a desired position during a CPR procedure. As such, the general purpose of the present invention, which will be described subsequently in greater detail, is to provide a new and improved resuscitation device which has all the advantages of the prior art resuscitation devices and none of the disadvantages.

To attain this, the present invention comprises a device defined by an upper angular mouthpiece including diametrically opposed flexible projections positioned on opposed edges of the mouthpiece for grasping by teeth of an administrator of the device. A first conduit is orthogonally oriented relative to the angular mouthpiece directed to a convex abutment skirt for engagement and positioning of a victim's mouth during use. A replaceable filter is removably mounted between the upper conduit and the skirt. A lower conduit in communication with the first conduit and filter and axially aligned therewith is of a generally arcuate "L" shaped configuration tapering downwardly to a lower opening. A modified filter for use with the invention includes a flexible squeeze bulb with a conduit associating the bulb with a filter, wherein the squeeze bulb includes a rupturable diaphragm containing a germicidal fluid therewith for directing the fluid onto the filter prior to use of the device. A further modified device includes an aspiration bulb of a generally pear shaped configuration formed with a tapered forward surface and a forward outlet for positioning within the mouthpiece to enable directing of pressurized air from the bulb through the first conduit, filter, and the lower conduit into a victim.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved resuscitation device which has all the advantages of the prior art resuscitation devices and none of the disadvantages.

It is another object of the present invention to provide a new and improved resuscitation device which may be easily and efficiently manufactured and marketed.

It is a further object of the present invention to provide a new and improved resuscitation device which is of a durable and reliable construction.

An even further object of the present invention is to provide a new and improved resuscitation device which is susceptible of a low cost of manufacture with regard to both materials and labor, and which accordingly is then susceptible of low prices of sale to the consuming public, thereby making such resuscitation devices economically available to the buying public.

Still yet another object of the present invention is to provide a new and improved resuscitation device which provides in the apparatuses and methods of the prior art some of the advantages thereof, while simultaneously overcoming some of the disadvantages normally associated therewith.

Still another object of the present invention is to provide a new and improved resuscitation device wherein the same utilizes a replaceable filter element and further utilizes optional germicidal fluid in use of the device preventing transmission of diseases from a victim.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an isometric illustration of the instant invention.

FIG. 4 is a side orthographic view taken in elevation of the instant invention.

FIG. 7 is an orthographic view taken in elevation of a modified filter segment utilized by the instant invention.

FIG. 8 is an isometric illustration of a modified resuscitation device utilized by the instant invention.

DESCRIPTION OF THE PREFERRED EMBODIMENT

Figure 1:
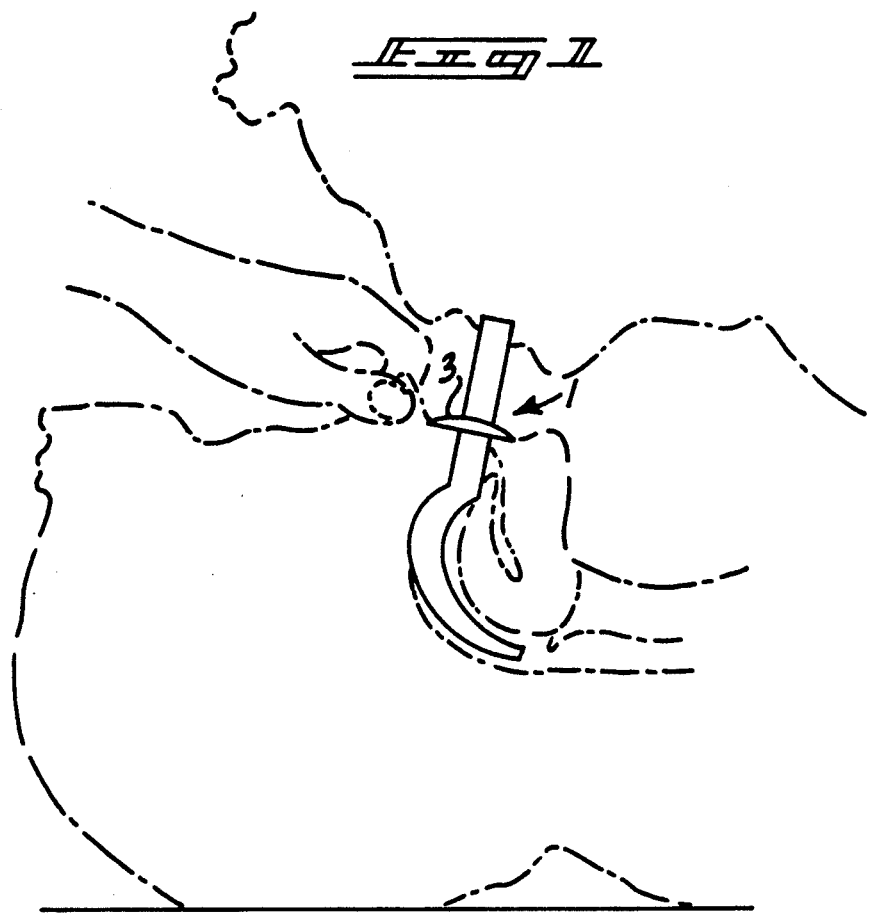
FIG. 1 is an orthographic side view taken in elevation of a prior art resuscitation device.

With reference now to the drawings, and in particular to FIGS. 1 to 8 thereof, a new and improved resuscitation device embodying the principles and concepts of the present invention and generally designated by the reference numerals 10 and 10a will be described.

Figure 2:
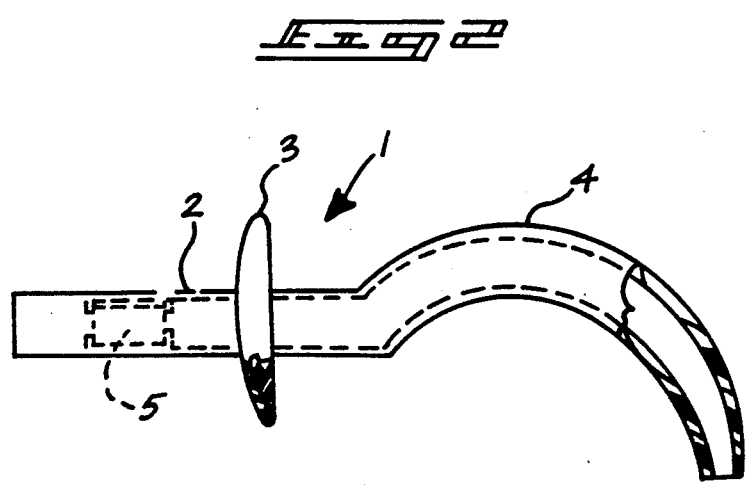
FIG. 2 is an orthographic side view of the resuscitation device as set forth in FIG. 1, enlarged for illustration of the details thereof.

More specifically, the resuscitation device of the instant invention comprises an improvement over the prior art resuscitation device 1, as illustrated in FIGS. 1 and 2. The device includes an upper conduit spaced from a lower, generally "C" shaped conduit with a mouth flange positioned orthogonally relative to the upper conduit, with a permanent filter member in a spaced relationship relative to an upper end of the upper conduit and the flange. The filter element 5 is of a permanent non-replaceable type and is therefore subject to breeding of various bacterial and viral diseases therewithin in use. Further, the filter element of the prior art is not accessible once secured therewith the upper conduit of the prior art device.

Figure 5:
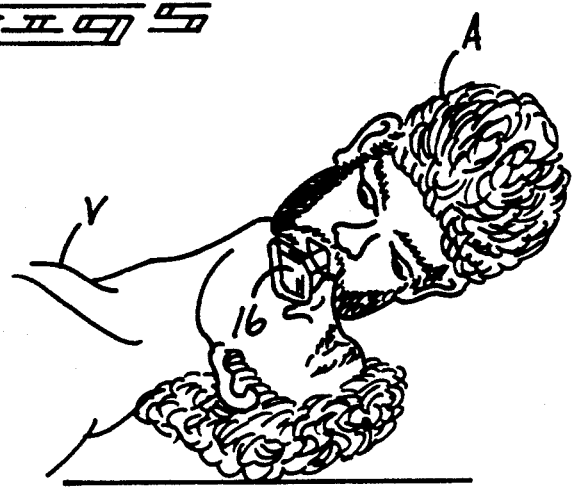
FIG. 5 is an isometric illustration of the instant invention in use.
Figure 6:
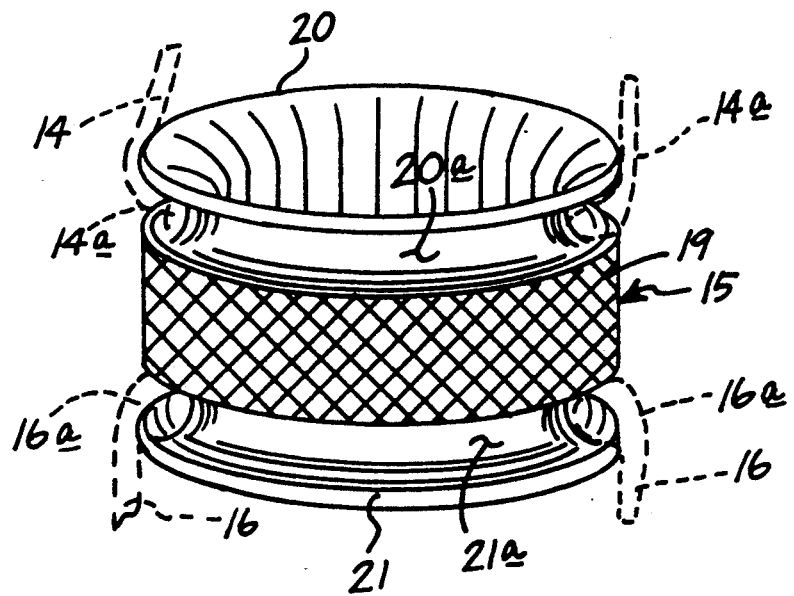
FIG. 6 is an isometric illustration of the replaceable filter segment of the instant invention.

More specifically, the resuscitation device 10 of the instant invention essentially comprises an elliptical mouthpiece 11 defining an inlet opening 11a wherein a first projection 12 and a second projection 13 are directed upwardly from the mouthpiece 11 diametrically opposed to one another along the major access of the elliptical mouthpiece 11 which in turn defines an elliptical inlet opening 11a. The projections include a central support 12a with an abutment cap 12b mounted orthogonally and integrally to an upper end of the central support 12a and extending beyond the central support to enable grasping of the central support by the teeth of an individual administrating CPR to a victim. Similarly, the second projection 13 includes a second central support 13a and a second abutment cap 13b of identical configuration to that of the first projection 12. The mouthpiece 11 includes an upper transparent conduit 14 coaxially and integrally mounted relative to the mouthpiece 11 and of a conduit diameter less than that defined by the mouthpiece, wherein the upper conduit 14 terminates at its lowermost end in a circumferential lip 14a, as illustrated in phantom in FIG. 6. A replaceable filter 15 is mounted to the circumferential lip 14a, wherein the filter 15 further is mounted at its lowermost end to a skirt lip 16a formed at an upper terminal end of an annular convex abutment skirt 16 directed exteriorly of the filter and of a skirt diameter greater than that defined by the filter, upper conduit, and mouthpiece 11. The skirt is of a flexible polymeric construction for overlying and positioning the lips of an individual, as illustrated in FIG. 5 for example. A lower conduit 17 of a generally "C" shaped configuration is axially aligned relative to the mouthpiece 11, upper conduit 14, filter 15, and skirt 16, and includes an outlet opening 18 at its lowermost end of a generally elliptical configuration for projection within an individual during a CPR procedure.

The filter 15 (see FIG. 6) is of a generally cylindrical configuration, including an upper "U" shaped flange 20 and a lower "U" shaped flange 21 coaxially aligned with a central filter body 19. Further, the upper "U" shaped flange 20 defines an upper "U" shaped channel 20a with the lower "U" shaped flange 21 defining a lower "U" shaped channel 21a to respectively receive the circumferential lip 14a of the upper conduit 14 and the skirt lip 16a respectively within the lower "U" shaped flange 21. It may be appreciated that the circumferential lip 14a and the skirt lip 16a are each of a flexible memory retentent material that enables replacement of the filter 15 and further provides a fluid and air-tight seal when the lips 14a and 16a are positioned within their associated "U" shaped channels.

Reference to FIG. 7 illustrates a modified filter 15a that includes a transparent, polymeric squeeze bulb 22 associated therewith, wherein the squeeze bulb 22 includes a generally spherical main body with a conduit 22a in fluid communication between the main body and the central filter body 19. The squeeze bulb 22 includes an internal membrane 23 coextensively formed as an interface between the main body of the bulb 22 and the associated conduit 22a. A liquid germicidal fluid 24 is contained within the main body of the bulb 22 whereupon squeezing of the main body results in a rupturing of the membrane 23 to enable directing of the fluid 24 into the central filter 19 to effect application of the germicidal fluid therethrough to minimize transmission of bacteria between a victim "V" and an administrator "A" of the device, as illustrated in FIG. 5.

A modified resuscitation device 10a, as illustrated in FIG. 8, sets forth a skirt 16a including a skirt aperture 25 formed therethrough adjacent a circumferential edge of the skirt, with a tether line 26 connecting the skirt 25 to an aspiration bulb 27 that is formed of a generally pear shaped configuration, with a spherical base 27b and a tapered forward end surface 27a terminating in a forwarding opening 28. To enable continued aspiration of a victim "V", the tapered forward end surface 27a is directed interiorly of the mouthpiece 11 into the conduit 14, wherein the tapered forward end surface 27a is of a length less than that defined by the axial length of the upper conduit 14 to enable continued aspiration and further minimize transmission of bacteria, virus, and the like between a victim and an administrator of the device.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A resuscitation device comprising,
    an elliptical mouthpiece defined by a major axis and a minor axis, and
    an upper conduit orthogonally and integrally mounted to the mouthpiece defined by an upper conduit diameter less than that defined by the major axis of a mouthpiece, and
    the upper conduit including a lower terminal end secured to an upper end of a cylindrical filter, and a lower terminal end of the cylindrical filter secured to an upper terminal end of an annular skirt, and
    the annular skirt defined by a skirt diameter, and
    a lower flexible conduit axially aligned with the upper conduit and filter and of a generally "C" shaped configuration terminating in an outlet opening, and
    wherein the skirt diameter is greater than that defined by the major axis, and the lower flexible conduit is defined by a conduit diameter less than that defined by the skirt diameter, and
    wherein the mouthpiece includes a first and second projection diametrically disposed relative to one another along the major axis of the mouthpiece, the first and second projection each including a central support integrally mounted to the mouthpiece, and wherein each central support includes an abutment cap integrally and orthogonally mounted thereon, wherein the abutment cap defines a flange extending beyond the central support to enable grasping of the central support by clenching teeth of an administrator of the device, and
    wherein the filter includes a central cylindrical filter body, and further includes an upper "U" shaped channel circumferentially mounted to an upper end of the central filter body, and a lower "U" shaped channel fixedly mounted to a lower end of the central filter body, and the upper "U" shaped channel selectively receiving a lower flange of the upper conduit, and the lower "U" shaped channel selectively receiving an upper flange defined by the upper terminal end of the annular skirt.

2. A device as set forth in claim 1 wherein the central filter body further includes a conduit in fluid communication therewith wherein the conduit is integrally mounted to a resilient flexible bulb member, the bulb member including a spherical central body, and a rupturable membrane defining an interface between the spherical body and the conduit, and the spherical body containing a predetermined quantity of a germicidal fluid therewithin.

3. A device as set forth in claim 2 wherein the skirt includes a skirt aperture positioned adjacent a peripheral edge of the skirt, and a tether line mounted to the skirt aperture at one of the tether line, and a pear shaped squeeze bulb, and the tether line secured to the pear shaped squeeze bulb at a further end of the tether line, and the pear shaped squeeze bulb including a cylindrical body and a tapered forward end surface, the tapered forward end surface of a length less than an axial length defined by the upper conduit, and the tapered forward end terminating in a forward opening receivable within the upper conduit in a sealing relationship between the forward end surface and the upper conduit to enable directing of pressurized air through the upper conduit and through the lower conduit from the pear shaped bulb.

* * * * *